United States Patent [19]

Leevy et al.

[11] Patent Number: 4,689,298
[45] Date of Patent: Aug. 25, 1987

[54] MALLORY BODY SPECIFIC MONOCLONAL ANTIBODY AND PROCESS FOR PRODUCING SAME

[75] Inventors: Carroll M. Leevy, Short Hills; Yoichi Sameshina, Cranford; Natarajan Kanagasundaram, Montville, all of N.J.

[73] Assignee: University of Medicine and Dentistry of NJ, Newark, N.J.

[21] Appl. No.: 643,290

[22] Filed: Aug. 22, 1984

[51] Int. Cl.$^4$ .......................... C07K 15/04; C12N 5/00
[52] U.S. Cl. ................................ 435/240.27; 435/68; 435/70; 435/172.2; 935/104; 530/387
[58] Field of Search ............... 260/112 R; 435/68, 70, 435/240, 172.2, 948, 241; 935/89, 93, 102–104, 99–100, 95; 436/548, 811, 820; 530/387

[56] References Cited
PUBLICATIONS

Morton, J. A. et al, *Gut,* vol. 22(1), pp. 1–7 (1981), cited in Chem. Abstract 95(1):4683j.
Morton, J. A. et al, *J. Pathology,* vol. 131(3), pp. 275–276 (1980), Cited in Bio. Abstract 20048097.
Burns, J. et al, *J. Clin. Pathol.,* vol. 36(7), pp. 751–755 (1983), cited in Bio. Abstract 77007757.
Sameshima, Y. et al, *Hepatology,* vol. 4(5), p. 1084 (1984), cited in Bio. Abstract 28044535.
Luisada-Opper et al, Chemical Nature of Alcoholic Hyalin, Gastroenterology 73:1374–1376, 1977.
Zetterman et al, Alcoholic Hepatitis, Gastroenterology 70:382–384, 1976.
Kanagasundaram et al, Immunologic Aspects of Liver Disease, Medical Clinics of North America, vol. 63, No. 3, May 1979, pp. 631–642.
McGee et al, Monoclonal Antibodies in Clinical Medicine, London Academic Press, 1982:431–455.
Leevy, et al, Immunologic Aspects of Liver Disease of the Alcoholic, Research Advances in Alcohol and Drug Problems, vol. 6, Plenum Publishing Corporation, 1981, pp. 255–280.
Sorrell et al, Lymphocyte Transformation and Alcoholic Liver Injury, Gastroenterology, vol. 63, No. 6 (1972), pp. 1020–1025.

*Primary Examiner*—Charles F. Warren
*Assistant Examiner*—M. Moskowitz
*Attorney, Agent, or Firm*—Weiser & Stapler

[57] ABSTRACT

There is disclosed a process for preparing anti-NMB-1 from Mallory bodies wherein Mallory bodies are removed and isolated from a liver and Mallory antibodies are produced by hybridoma techniques followed by isolation of the anti-NMB-1 having two polypeptide components of 45 and 66 kd by Western blotting.

2 Claims, 2 Drawing Figures

A. High Molecular Weight Standards
B. Mallory Body
C. Western Blotting of anti-NMB-1 on Mallory Body
D. Low Molecular Weight Standards

MALLORY BODY SPECIFIC MONOCLONAL ANTIBODY AND PROCESS FOR PRODUCING SAME

FIELD OF THE INVENTION

This invention relates to monoclonal antibodies, and more particularly to a Mallory body specific monoclonal antibody.

BACKGROUND OF THE INVENTION

Mallary bodies, a pinkish structureless material in hematoxylineosin stained sections are found in many liver diseases including alcoholic hepatitis, cirrhosis, hepatocellular cancer. When isolated and purified immunologic studies demonstrate lymphocytes sensitized to Mallory bodies are cytotoxic and elaborate fibrogenic, migration inhibition, chemotactic, cholestatic and transfer factors. Availability of a specific, sensitive immunoassay for Mallory bodies and their antibodies would allow detection of early phase liver injury associated with this protein, facilitate monitoring of effect of treatment. Using complement fixation and immune hemagglutination tests MBAg and MBAb were demonstrated in various phases of alcoholic hepatitis, the precursion of alcoholic cirrhosis. This led to the use of standard techniques to produce monoclonal antibodies to Mallory bodies, however, none of which reacted only with Mallory bodies.

OBJECT OF THE INVENTION

An object of the present invention is to produce a specific Mallory body monoclonal antibody.

Another object of the present invention is to provide a process for purifying an antigenic moiety in a Mallory body.

Yet another object of the present invention is to provide a process for purifying an antigenic moeity in a Mallory body which when added to sensitized lymphocytes stimulates blastogenesis, increased MIF production, blocked cytotoxicity and evoked fibrogenesis.

SUMMARY OF THE INVENTION

These and other objects of the present invention are attained by a process for preparing anti-NMB-1 from Mallory bodies wherein Mallory bodies are removed and isolated from a liver and Mallory antibodies are produced by hybridoma techniques followed by isolation of the anti-NMB-1 having two polypeptide components of 45 and 66 kd by Western blotting.

DESCRIPTION OF THE INVENTION

Mallory bodies were isolated with special attention to preserving the antigenicity of the preparation. Post mortem livers are obtained from patients who succumb to alcoholic hepatitis and having minimum fibrosis, large amounts of Mallory bodies and absence of a history of any addictions. The liver is obtained within 24 hours after death, sliced and stored at $-70°$ C. Isolation of Mallory bodies is carried out by centrifugation and filtration using Ficoll gradient at about $4°$ C.

The liver slices are homogenized in an isolation medium (e.g. 0.8M sucrose, 5 mM Tris, 5 mM EDTA, 1 mM DDT, 0.1 mM PMSF, and 1 mM Sodium Azide—pH 7.5). The suspensions are filtered, respectively, through surgical gauze and glass wool, and then centrifuged. The resulting pellets are resuspended in the isolation medium and further homogenized. Thereafter, the suspension is subjected to discontinuous Ficoll gradient centrifugation and the pellet and Ficoll layer are checked for purity.

Figure 1:
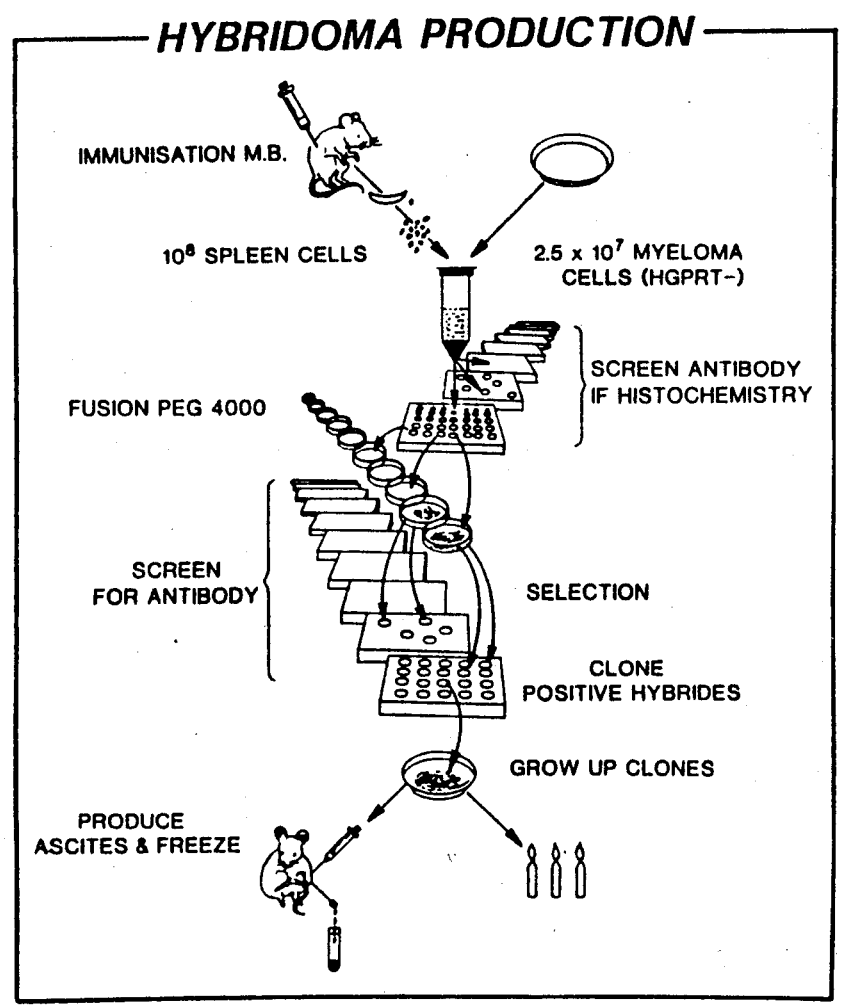
FIG. 1 is a schematic flow diagram of a standard hybridoma technique.

Purified monoclonal anti-NMB-1 is produced by standard hybridoma techniques and obtained from ascitic fluid induced by intraperitoneal injections of hybrids, referring to FIG. 1. Mice are immunized with 100 mg of freshly prepared non denatured isolates of Mallory bodies in Freund's complete adjuvant. Fusions are carried out between spleen cells of selected antibody-producing mice and $\times 63$ Ag 8.6. 5.3 myeloma cells. Using immune histochemical techniques binding by anti-NMB-1, an IgM immunoglobulin was limited to Mallory bodies.

Figure 2:
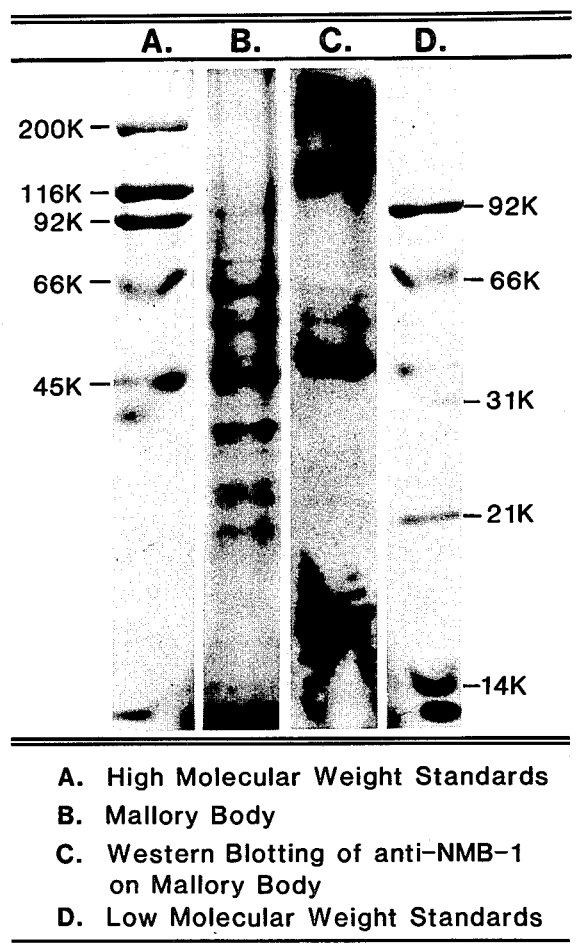
FIG. 2 is the results of Western blotting.

The antigenic site in Mallory bodies isolates to anti-NMB-1 is revealed to exist in two polypeptide components of 45 and 66 kd by Western blotting, referring to FIG. 2. The antigenicity is lost after 2 to 6 days storage at $4°$ C.

Anti-NMB-1 is not reactive with filaments structures in non Mallory body containing tissues thus permitting its use for specific Mallory body immunoassays. Anti-NMB-1 reacted to two polypeptide bands at 45 and 66 kd of Mallory body isolate.

Numerous modifications and variations of the present invention are possible in light of the above teachings and, therefore, within the scope of the appended claims, the invention may be practiced otherwise than as particularly described.

What is claimed:

1. A hybridoma, NMB-1, which expresses monoclonal antibodies which bind with an antigenic site in Mallory bodies only.

2. A monoclonal antibody which binds with an antigenic site in Mallory bodies only and is expressed by NMB-1.

* * * * *